(12) United States Patent
Wensrich

(10) Patent No.: US 11,324,589 B2
(45) Date of Patent: May 10, 2022

(54) INTRAOCULAR LENS INJECTOR

(71) Applicant: Alcon Inc., Fribourg (CH)

(72) Inventor: Douglas Brent Wensrich, Bedford, TX (US)

(73) Assignee: Alcon Inc., Fribourg (CH)

( * ) Notice: Subject to any disclaimer, the term of this patent is extended or adjusted under 35 U.S.C. 154(b) by 251 days.

(21) Appl. No.: 16/507,144

(22) Filed: Jul. 10, 2019

(65) Prior Publication Data

US 2020/0015957 A1    Jan. 16, 2020

Related U.S. Application Data

(60) Provisional application No. 62/696,084, filed on Jul. 10, 2018.

(51) Int. Cl.
    *A61F 2/16*     (2006.01)

(52) U.S. Cl.
    CPC ............ *A61F 2/167* (2013.01); *A61F 2/1678* (2013.01); *A61F 2002/1683* (2013.01)

(58) Field of Classification Search
    CPC ................... A61F 2/167; A61F 2/1678; A61F 2002/1683; A61F 2250/0007; A61F 2250/0065; A61M 2005/2086; A61M 2005/2418; A61M 2005/3143; A61M 2206/22

See application file for complete search history.

(56) References Cited

U.S. PATENT DOCUMENTS

| | | | |
|---|---|---|---|
| 7,156,854 B2 | 1/2007 | Brown et al. | |
| 2010/0106160 A1* | 4/2010 | Tsai | A61F 2/167 |
| | | | 606/107 |
| 2010/0125278 A1* | 5/2010 | Wagner | A61F 2/1662 |
| | | | 606/107 |
| 2016/0256316 A1 | 9/2016 | Van Noy et al. | |
| 2017/0172727 A1* | 6/2017 | Kanner | A61F 2/167 |

FOREIGN PATENT DOCUMENTS

| | | |
|---|---|---|
| EP | 2491902 A1 | 8/2012 |
| WO | 9637152 A1 | 11/1996 |

* cited by examiner

*Primary Examiner* — Tan-Uyen T Ho
*Assistant Examiner* — Chima U Igboko

(57) ABSTRACT

IOL injectors and associated methods are described. An IOL injector may include a collapsible portion configured to reduce the length of the IOL injector when the collapsible portion is altered from an uncollapsed configuration to a collapsed configuration. In some instances, an IOL may be advanced from a storage location to a dwell location when the collapsible portion is altered from the uncollapsed configuration to the collapsed configuration. An IOL injector may include one or more of a hydraulic damper and a ribbed damper.

5 Claims, 9 Drawing Sheets

INTRAOCULAR LENS INJECTOR

CROSS-REFERENCE TO RELATED APPLICATIONS

This application claims the benefit of U.S. Provisional Application No. 62/696,084, filed Jul. 10, 2018, the entire contents of which are incorporated herein by reference.

TECHNICAL FIELD

The present disclosure relates to ophthalmic surgery, and more specifically, to an intraocular lens (IOL) injector.

BACKGROUND

In ophthalmology, eye surgery, or ophthalmic surgery, saves and improves the vision of tens of thousands of patients every year. However, given the sensitivity of vision to even small changes in the eye and the minute and delicate nature of many eye structures, ophthalmic surgery is difficult to perform and the reduction of even minor or uncommon surgical errors or modest improvements in accuracy of surgical techniques can make an enormous difference in the patient's vision after the surgery.

Light enters the human eye through a clear cornea that is located on the outer part of the eye and covers the pupil and iris. The light travels through the pupil and then encounters the lens, located behind the iris. As the light travels through the lens, the lens refracts the light so that it focuses on the retina, located in the back of the eye. Special cells in the retina detect the light and transmit signals based on the light via the optic nerve to the brain, which interprets the signals as vision.

Vision quality is, therefore, influenced by a number of factors, including the transparency and refractive properties of the cornea and the lens. Unfortunately, as people age or due to trauma or disease, the lens may be become less transparent and a cataract develops. Cataracts cause deterioration of vision and are often surgically corrected. During some cataract surgeries, the lens is surgically removed and replaced with an artificial intraocular lens (IOL).

Many cataractous lenses are removed by a surgical technique called phacoemulsification. During this procedure, an opening is made in the anterior capsule and a phacoemulsification cutting tip is inserted into the diseased lens and vibrated ultrasonically. The vibrating cutting tip liquefies or emulsifies the lens so that the lens may be aspirated out of the eye. The diseased lens, once removed, is replaced by an artificial lens, also referred to as an intraocular lens (IOL).

The IOL is injected into the eye through a small incision, sometimes the same incision used to remove the diseased lens. An IOL injector is used to deliver an IOL into the eye.

SUMMARY

According to a first aspect, the present disclosure relates to an intraocular lens (IOL) injector having a collapsible injector body configured to reduce a length of the IOL injector upon an advancement of an IOL from a storage location to a dwell location. The IOL injector may include an injector body and a plunger received into and movably within the injector body. The injector body may include a main body having a proximal end and a distal end and defining a passage therethrough; an IOL storage compartment formed in the main body, the storage compartment adapted to store an IOL in a storage location; a nozzle coupled to the distal end of the main body; and a collapsible portion disposed between the main body and the nozzle, the collapsible portion moveable between a collapsed configuration and an uncollapsed configuration. The nozzle may include a bore and a distal opening in fluid communication with the bore. The collapsible portion may include a first sleeve and a second sleeve telescopingly received into the first sleeve. The collapsible portion may be moveable from the uncollapsed configuration in which the first sleeve is at a first position relative to the second sleeve to the collapsed configuration in which the first sleeve is at a second position relative to the second sleeve. The plunger tip may move from a first plunger tip location to a second plunger tip location distal of the first plunger tip location when the collapsible portion is moved from the uncollapsed configuration to the collapsed configuration.

According to a second aspect, the present disclosure relates to an IOL injector that may include an injector body; a hydraulic damper disposed within the injector body; and plunger. The injector body may include a main body having a proximal end and a distal end; an IOL storage compartment formed in the main body, the storage compartment adapted to store an IOL in a storage location; a bore; and a distal opening in fluid communication with the bore. The hydraulic damper may include a first cylinder, a second cylinder, a restrictor disposed between the first cylinder and the second cylinder, and a fluid moveable between the first cylinder and the second cylinder via the restrictor. The first cylinder, the second cylinder, and the restrictor may form a passage. The restrictor may include an orifice and a distal chamber in fluid communication with the orifice, the distal chamber having a conical shape. The plunger may include a body portion disposed in the second cylinder and a plunger rod disposed in the first cylinder, the plunger rod moveable within the first cylinder in response to displacement of fluid from the second cylinder to the first cylinder in response to movement of the plunger body in the second cylinder.

According to a third aspect, the present disclosure relates to an IOL injector that may include an injector body; a plunger; and a ribbed damper. The injector body may include a main body defining a bore and comprising a proximal end and a distal end; an IOL storage compartment formed in the main body, the storage compartment adapted to store an IOL in a storage location; and a nozzle coupled to the distal end of the main body. The nozzle may include a bore and a distal opening in fluid communication with the bore. The plunger may be disposed in the bore and be moveable therein. The ribbed damper may include a first rib formed on an internal surface of the bore and a second rib formed on an exterior surface of the plunger. The first rib may have a wedge shape that increases in size from a proximal end to a distal end, and the second rib may have a wedge shape that increases in size from a distal end to a proximal end. The first rib and the second rib may be adapted to increase a resistance to an axial movement of the plunger within in the bore.

The various aspects may include one or more of the following features. The first plunger tip position may be proximal to the storage location, and the plunger tip may be adapted to engage an IOL disposed in the storage portion and move the IOL from the storage location within the storage compartment to a dwell location within the nozzle when the collapsible portion is moved from the uncollapsed configuration to the collapsed configuration. The first sleeve may be concentrically disposed within the second sleeve. The second sleeve may be concentrically disposed within the first sleeve. A hydraulic damper may be disposed within the injector body. The hydraulic damper may include a first cylinder, a second cylinder, and a restrictor disposed between the first cylinder and the second cylinder. The restrictor comprises an orifice in fluid communication with the first cylinder and the second cylinder. The plunger may include a body portion received and slideable within the second cylinder and a plunger tip received and slideable with the first cylinder. The hydraulic damper may also include a fluid disposed between a proximal end of the plunger tip and a distal end of the body portion. The first cylinder may have a first cross-sectional size, and the second cylinder may have a second cross-sectional size. The first cross-sectional size may be larger than the second cross-sectional size.

The various aspects may also include one or more of the following features. The restrictor may include an orifice in fluid communication with the first cylinder and the second cylinder. A collapsible portion may also be included. The collapsible portion may include a first sleeve and a second sleeve telescopingly received into the first sleeve. Movement of the second sleeve into the first sleeve may displace the plunger tip from a first position to a second position distal of the first position. Movement of the plunger tip from the first position to the second position may be operable to displace the IOL from the storage location to a dwell location in the nozzle. The first rib and the second rib may cooperate to permit movement of the plunger in a first direction but prevent movement of the plunger in a second direction opposite the first direction. The first rib may be circumferentially continuous on the exterior surface of the plunger rod. The second rib may be circumferentially continuous on the interior surface of the bore. A collapsible portion may be disposed between the main body and the nozzle and may be moveable between a collapsed configuration and an uncollapsed configuration. The collapsible portion may include a first sleeve and a second sleeve telescopingly received into the first sleeve. The plunger may include a plunger tip. Moving the collapsible portion from the uncollapsed configuration in which the first sleeve is at a first position relative to the second sleeve to the collapsed configuration in which the first sleeve is at a second position relative to the second sleeve may be operable to displace the plunger tip from a first plunger tip location to a second plunger tip location distal of the first plunger tip location.

BRIEF DESCRIPTION OF THE DRAWINGS

For a more complete understanding of the present disclosure and the associated features and advantages, reference is now made to the following description, taken in conjunction with the accompanying drawings, which are not to scale, and in which.

DETAILED DESCRIPTION

Figure 1:
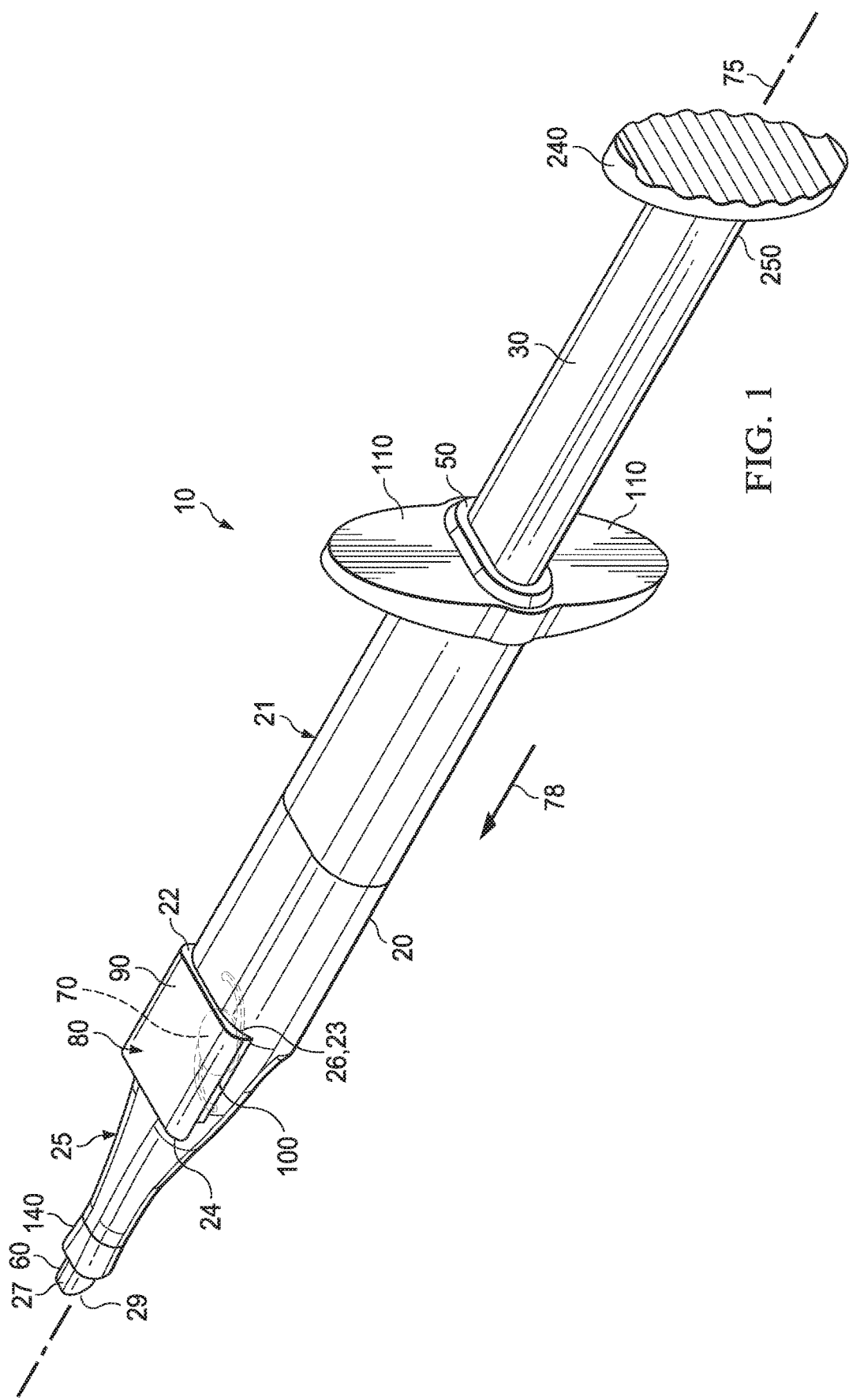
FIG. 1 is a perspective view of an example IOL injector.

In the following description, details are set forth by way of example to facilitate discussion of the disclosed subject matter. It should be apparent to a person of ordinary skill in the art, however, that the disclosed implementations are exemplary and not exhaustive of all possible implementations.

For the purposes of promoting an understanding of the principles of the present disclosure, reference will now be made to the implementations illustrated in the drawings, and specific language will be used to describe the same. It will nevertheless be understood that no limitation of the scope of the disclosure is intended. Any alterations and further modifications to the described devices, instruments, methods, and any further application of the principles of the present disclosure are fully contemplated as would normally occur to one skilled in the art to which the disclosure relates. In particular, it is fully contemplated that the features, components, and/or steps described with respect to one implementation may be combined with the features, components, and/or steps described with respect to other implementations of the present disclosure.

The present disclosure relates to ophthalmic surgery and, more specifically, to an intraocular lens (IOL) injector.

Following removal of a cataractous lens by phacoemulsification, the cataractous lens is replaced by an artificial lens, referred to herein as an intraocular lens (IOL). The IOL is typically injected into the eye through the same small incision used to remove the diseased lens. An IOL injector is used to deliver an IOL into the eye.

Figure 2:
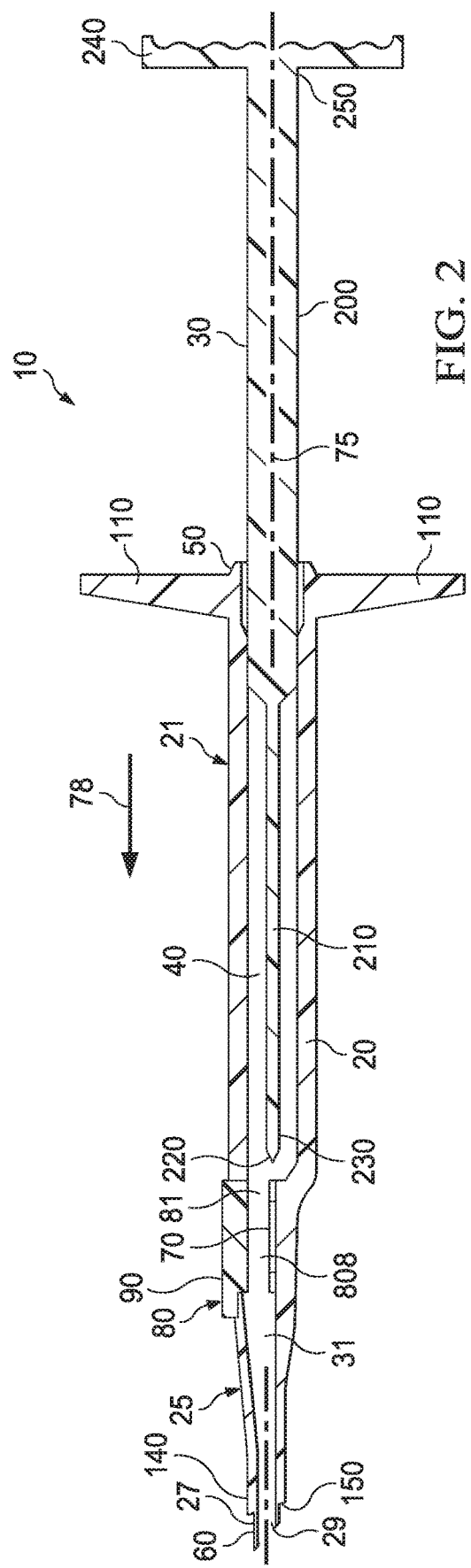
FIG. 2 is a longitudinal cross-sectional view of the exemplary IOL injector of FIG. 1.

FIGS. 1 and 2 are schematics of an exemplary IOL injector 10. The IOL injector 10 includes an injector body 20. The injector body 20 includes a main body 21 having a proximal end 50 and a distal end 22. The injector body 20 includes an injector nozzle 25 having a proximal end 23 and a distal end 60. The nozzle 25 defines a passage 31. The proximal end 23 of the injector nozzle 25 is coupled to the distal end 22 of the main body 21. A proximal portion of the nozzle 25 includes an IOL storage compartment 80 that defines a cavity 81 operable to house an IOL 70 prior to insertion into an eye. The nozzle 25 also includes a distal tip 27 that defines an opening 29 through which the IOL is delivered out of the IOL injector 10. In some implementations described herein, the storage compartment 80 defines an IOL storage location 808. The IOL storage compartment 80 has a proximal end 26 and a distal end 24, the proximal end 26 of the IOL storage compartment 80 being coupled to the distal end 22 of the main body 21. In some instances, a door 90 may be included to provide access to the IOL storage compartment 80. The door 90 may include a hinge 100 such that the door 90 may be pivoted about the hinge 100 to open the IOL storage compartment 80. The injector body 20 defines a bore 40 that joins and is fluid communication with the opening 29. A longitudinal axis 75 extends along the bore 40. The injector body 20 may also include tabs 110, for example formed at the proximal end 50 of the main body 21. Other configurations are possible. For example, in other implementations, the tabs 110 may be located at the distal end 22 of the main body 21. The tabs 110 may be manipulated by fingers of a user, such as an ophthalmologist or other medical professional, to advance a plunger 30 (discussed below) through the bore 40.

In some implementations, various manipulations of the IOL injector 10, and various method steps, may be performed by one person, or by a plurality of persons. For example, some steps of methods described herein may be performed by a nurse, while other steps may be performed by an ophthalmic surgeon. For example, advancing an IOL 70 within the injector body 20 of an IOL injector 10 from a storage location 808 to a dwell location 809 (as shown, for example, in FIG. 9) may be performed by a nurse, while injection of the IOL 70 into an eye may be performed by a surgeon.

The IOL injector 10 also includes a plunger 30 received within the bore 40 and moveable therein such that the plunger 30 is slideable within the bore 40. As the plunger 30 is displaced distally within bore 40, the plunger 30 engages and advances an IOL, such as IOL 70, contained in the compartment 80.

As shown in FIG. 2, the plunger 30 includes a body portion 200, a plunger rod 210 extending distally from the body portion 200, and a plunger tip 220 formed at a distal end 230 of the plunger rod 210 and adapted to contact an IOL disposed, for example, within the IOL storage compartment 80 of the IOL injector 10. The plunger 30 may also include a flange 240 formed at a proximal end 250 of the body portion 200. The plunger 30 is movable along the bore 40 in response to an axial force applied to the plunger 30 in the direction of arrow 78. The axial force may be applied to the flange 240, such as by a thumb of a user.

In some implementations described herein, various parts of the plunger 30 may be physically separated or decoupled from each other within the injector body 20 of the IOL injector 10. For example, in some implementations, the body portion 200 may be physically separated or decoupled from the plunger rod 210. In various implementations, where various parts of the plunger 30 are physically separated or decoupled from each other, additional components of the IOL injector 10 may actuate movement of one part of the plunger 30 in response to movement of another part of the plunger 30.

Figure 3:
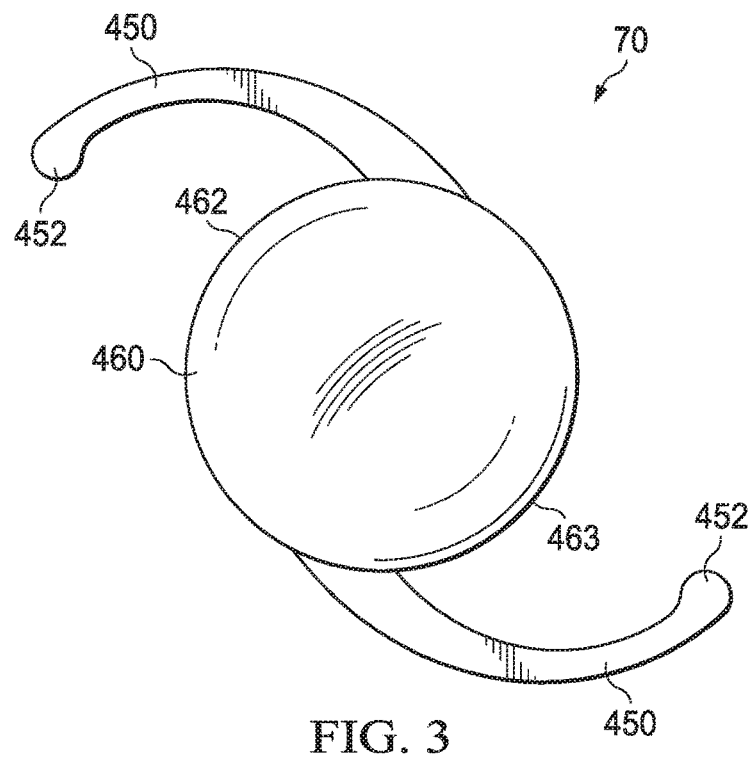
FIG. 3 shows an exemplary one-piece IOL.

In some implementations, the IOL 70 may be a one-piece IOL. That is, in some implementations, the IOL 70 may include an optic 460 and haptics 450, as shown in FIG. 3. Each of the haptics 450 includes a tip 452. In some implementations, the optic 460 and the haptics 450 may be integrally formed out of a single piece of material. In other implementations, the optic 460 may be formed out of one piece of material; the haptics 450 may be formed out of another piece of material; and the optic 460 and the haptics 450 may be coupled together prior to delivery into an eye. In some instances, the optic 460 and haptics 450 may be fixedly secured to each other prior to insertion into an IOL injector and delivered into an eye. The optic 460 includes a distal edge 462 and a proximal edge 463.

Figure 4:
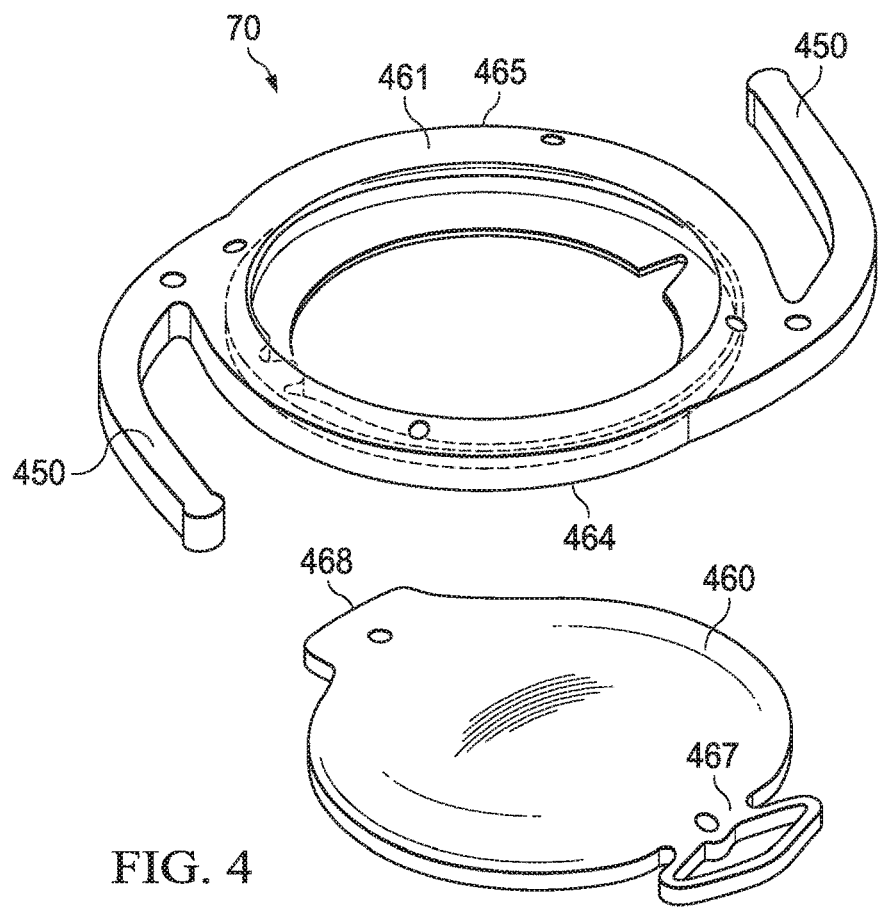
FIG. 4 shows an exemplary two-piece IOL including a base and an optic.

In other implementations, the IOL 70 may be a multi-piece IOL. For example, in some implementations, the IOL 70 be include two or more separate components. FIG. 4 is an example two-piece IOL 70 that includes two removably attached components. As shown in FIG. 4, the IOL 70 includes an optic 460 and a base 461 that includes haptics 450. The optic 460 and the base 461 are adapted to be coupled together into a unitary IOL and, thereafter, detached from each other into separate components, if desired. In some instances, one or more components of a multi-piece IOL, such as, for example the two-piece IOL 70 shown in FIG. 4, are separately injectable into a patient's eye. Once in the eye, the components may be assembled into a complete IOL. For example, for the two-piece IOL 70 shown in FIG. 4, the optic 460 and the base 461 are separately injectable into an eye. Once injected, the optic 460 is adapted to be coupled to and to rest on the base 461. The base 461 includes a distal edge 464 and a proximal edge 465. The optic 460 includes a distal edge 467 and a proximal edge 468.

Occasionally, patients may require replacement of an IOL, and a procedure to replace an IOL may result in damage to the eye. With the use of a two-piece IOL, for example, a replacement procedure may involve replacement only of the optic, allowing the base to remain in place within the eye.

As explained above, in some implementations, the IOL 70 may be a two-piece IOL wherein the base 461 and the optic 460 are separately injected into the patient's eye. Accordingly, for two-piece IOLs, the base 461 and the optic 460 may be contained in separate IOL injectors 10 for insertion in the eye. In other implementations, the two components of a two-piece IOL may be inserted into an eye separately using a single IOL injector. For a single-piece IOL, the optic 460 and haptics 450 form a unitary IOL and are inserted into an eye simultaneously with the use of a single IOL injector.

Accordingly, in some implementations, a user may place a one-piece IOL into an IOL injector, for example, by loading an IOL into the IOL storage compartment of the IOL injector, such as the IOL storage compartment 80 of the IOL injector described above. As also explained, the storage compartment may be accessed via a door, such as the door 90. In some implementations, the IOL may be manually folded into a compressed or folded configuration prior to installation into the IOL injector.

In the case of a two-piece IOL, in some implementations, a user may load the base (which may be similar to base 461) into an IOL storage compartment of an IOL injector, for example, via a door. The optic (which may be similar to optic 460) of may be introduced into the IOL storage compartment of separate IOL injector, for example, via a door. In some instances, the IOL storage compartment may be accessed through the door similar to door 90. In some implementations, one or both of the base and the optic may be manually folded into a compressed or folded configuration prior to installation into an IOL injector.

In some implementations, the IOL may be pre-loaded into the storage compartment of an IOL injector, for example, during manufacturing or otherwise prior to distribution to an end user. Accordingly, for the one-piece IOL, the one-piece IOL may be pre-loaded into the storage compartment an IOL injector prior to receipt by the end user. For a two-piece IOL, the base may be pre-loaded into a storage compartment of one IOL injector, while the optic may be pre-loaded into the IOL storage compartment of another IOL injector. The term "pre-loaded" as used herein means that an IOL, either in a one-piece or multi-piece configuration (including, for example, a two-piece configuration), is loaded into the IOL injector not by a user, but, rather, the IOL is installed and already contained within the IOL injector when the IOL injector is received by the user. The IOL injector(s) may be packaged within sterile packaging when received by a user.

As would be understood by persons of ordinary skill in the art, an IOL that is pre-loaded into an IOL injector has advantages over manual installation and folding of an IOL into the IOL injector that is performed by a user. For example, manual installation and folding of an IOL may allow more opportunity for errors, which have the potential to cause unnecessary secondary manipulation or correction during an already complex procedure. Manual installation and folding of an IOL may also introduce the possibility of contamination of the IOL, such as by human error or poor sterile technique. Contamination of the IOL may compromise the sterile environment for the patient and risk infection or other harm to the patient.

Figure 5:
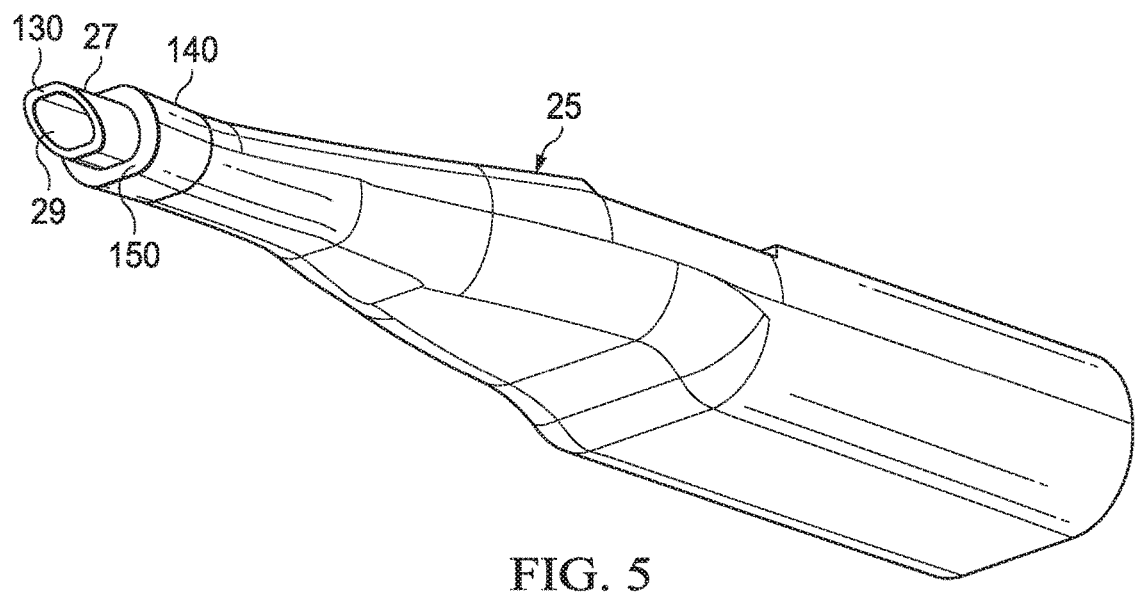
FIG. 5 is a perspective view of an exemplary nozzle of an IOL injector.
Figure 6:
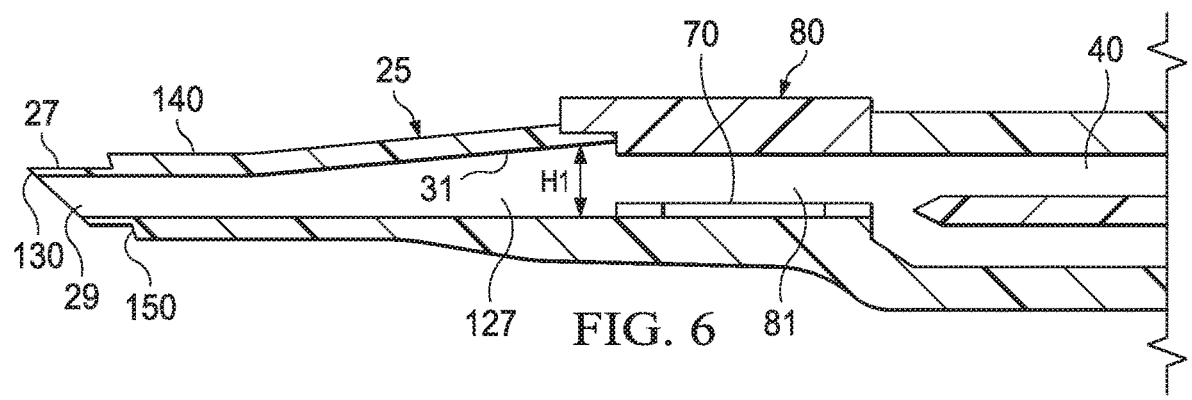
FIG. 6 is a cross-sectional view of the exemplary nozzle of an IOL injector shown in FIG. 5.
Figure 7:
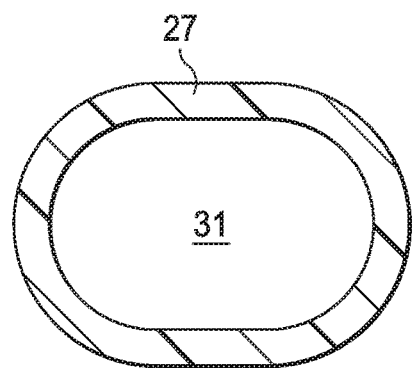
FIG. 7 is an exemplary cross-sectional view of a distal tip of a nozzle of an IOL injector.

FIGS. 5-7 illustrate details of the exemplary nozzle 25. In some instances, the nozzle 25 has a tapered exterior surface. Further, the passage 31 of the nozzle 25 may form part of the bore 40. The passage 31 tapers towards the opening 29. The distal tip 27 is adapted for insertion into an eye so that an IOL may be implanted. An IOL is expelled from the opening 29 formed in the distal tip 27. As shown in FIG. 7, the distal tip 27 may have an elliptical cross section. Additionally, the distal tip 27 may include a beveled tip 130. The cavity 81 of the storage compartment 80, passage 31, and opening 29 may define a delivery passage 127. A size of the delivery passage 127 may vary along a length thereof. That is, in some instances, a height H1 of the delivery passage 127 may change along a length thereof. The variation in size of the delivery passage 127 may contribute to the folding of the IOL as it is advanced therealong.

In some instances, the injector body 20 may include an insertion depth guard 140. The insertion depth guard 140 may form a flanged surface 150 that is adapted to abut an exterior eye surface. The insertion depth guard 140 abuts an eye surface and, thereby, limits an amount by which the distal tip 27 is permitted to extend into an eye, as described in U.S. application Ser. No. 15/049,315, the disclosure of which is being incorporated herein by reference in its entirety.

Figure 8:
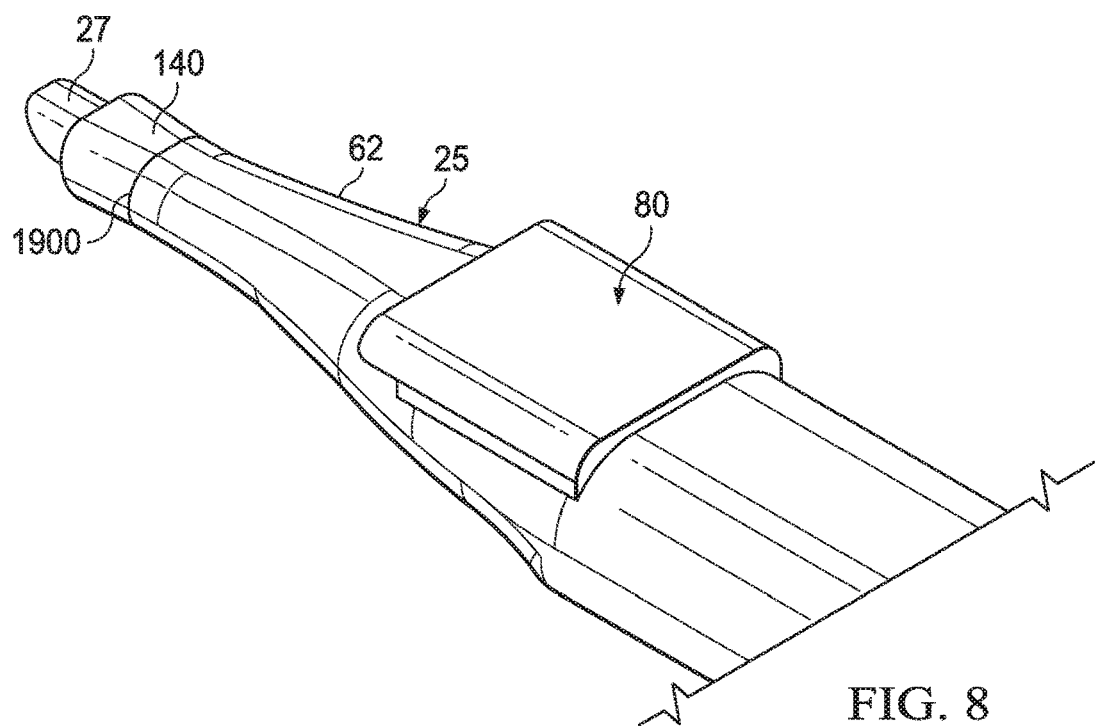
FIG. 8 is a detail view of an exemplary nozzle.

FIG. 8 is a detail view of a portion of the exemplary nozzle 25. The nozzle 25 may include a tapered portion 62 and the insertion depth guard 140. The distal tip 27 may include a demarcation 1900 that provides a visual indication of the dwell location 809 (shown, for example, in FIG. 9) of the folded or partially folded IOL 70. The term "dwell location" as used herein refers to a location adjacent to the distal end 60 of the nozzle 25 where an IOL would reside prior to being ejected from the IOL injector. For example, in some implementations, the dwell location 809 may be a location between 2 mm and 10 mm from the distal end 60. An IOL may be placed in dwell location prior to a surgical procedure. The IOL may be placed in the dwell location such as by a nurse or other medical professional that prepares the IOL injector for use. Placing an IOL in a dwell location provides for folding an IOL, either partially or fully, and for a decreased travel distance of the IOL when a physician takes possession of the IOL for implantation of the IOL into a patient's eye. Thus, placing an IOL placed at the dwell location may be a preparatory step performed by an assistant to a surgical procedure that allows the physician more quickly to perform the surgical procedure once the physician takes possession of the IOL injector. For example, in the example shown in FIG. 8, the demarcation 1900 is a narrow ridge or line that encircles all or a portion of the nozzle 25.

In some instances, the demarcation 1900 may be formed into the nozzle 25, such by a recess or groove or a protruding ridge. In other implementations, the demarcation 1900 may be formed by a paint or other coating or an additive or insert applied to the material forming the nozzle 25, such as during manufacturing or sometime thereafter. In some instances, the demarcation 1900 may be disposed between the tapered portion 62 and the insertion depth guard 140. In implementations in which a depth guard 140 is omitted, the demarcation 1900 may located between the distal tip 27 and the tapered portion 62. At least a portion of the injector body 20 may be formed from a transparent or semi-transparent material that permits a user to see an IOL within the injector body 20. Particularly, the nozzle 25 of the injector body 20 may be formed from a transparent material to permit observation of the IOL as the IOL is moved therethrough by the plunger 30.

Figure 9:
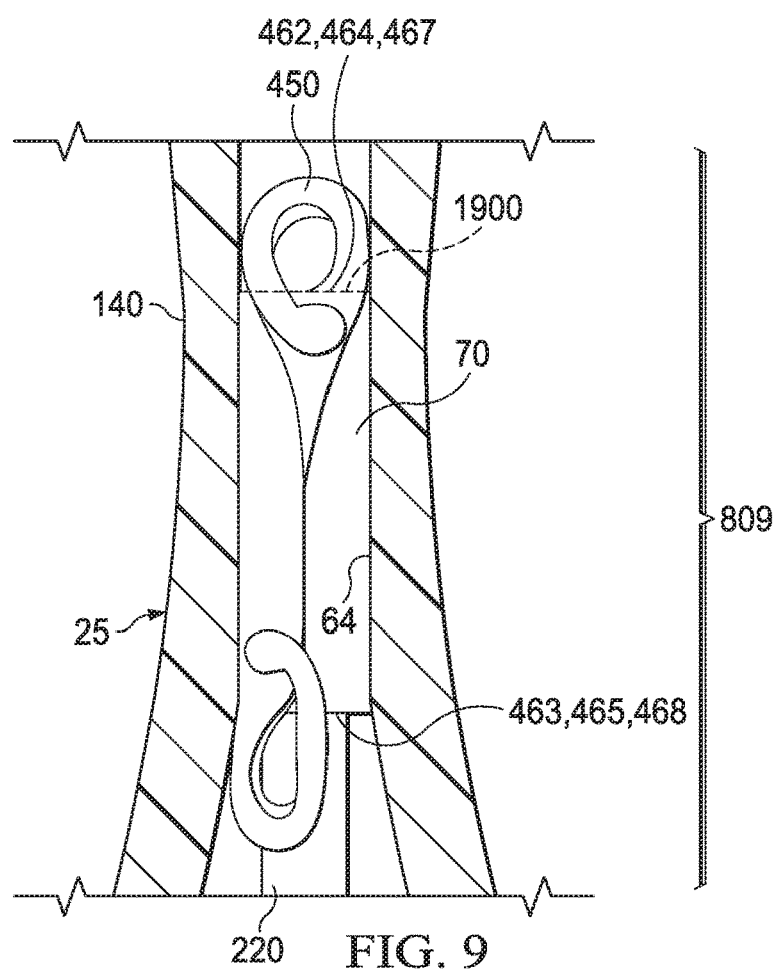
FIG. 9 is another detail view of a cross-section of an exemplary nozzle showing an IOL located at a dwell location.

FIG. 9 shows a view of the exemplary nozzle 25 with the IOL 70 located therein at the dwell location 809. A plunger 220 is shown contacting the proximal edge 463, 465, or 468. As shown in FIG. 9, the dwell location 809 of the IOL 70 may be defined as a location where a distal edge 462 of the optic 460 of the IOL 70 aligns with the demarcation 1900. In the case of a two-piece IOL, such as IOL 70 shown in FIG. 4, where the base 461 and optic 460 are implanted into an eye separately, the dwell location 809 of the two-piece IOL 70 may be defined as a location where a distal edge 467 of the optic 460 or the distal edge 464 of the base 461 aligns with the demarcation 1900. A haptic 450 or a portion thereof may extend beyond the demarcation 1900. Further, although FIG. 9 shows the IOL 70 as including haptics 450, it is understood that the IOL 70 shown in FIG. 9 may also represent the optic 460 of a two-piece IOL, such as the two-piece IOL 70 shown in FIG. 4, which omits haptics.

In implementations described herein, the IOL injector 10 may include a collapsible injector body configured to reduce the length of the IOL injector upon an advancement of the IOL 70 from the storage location 808 to the dwell location 809.

Figure 10:
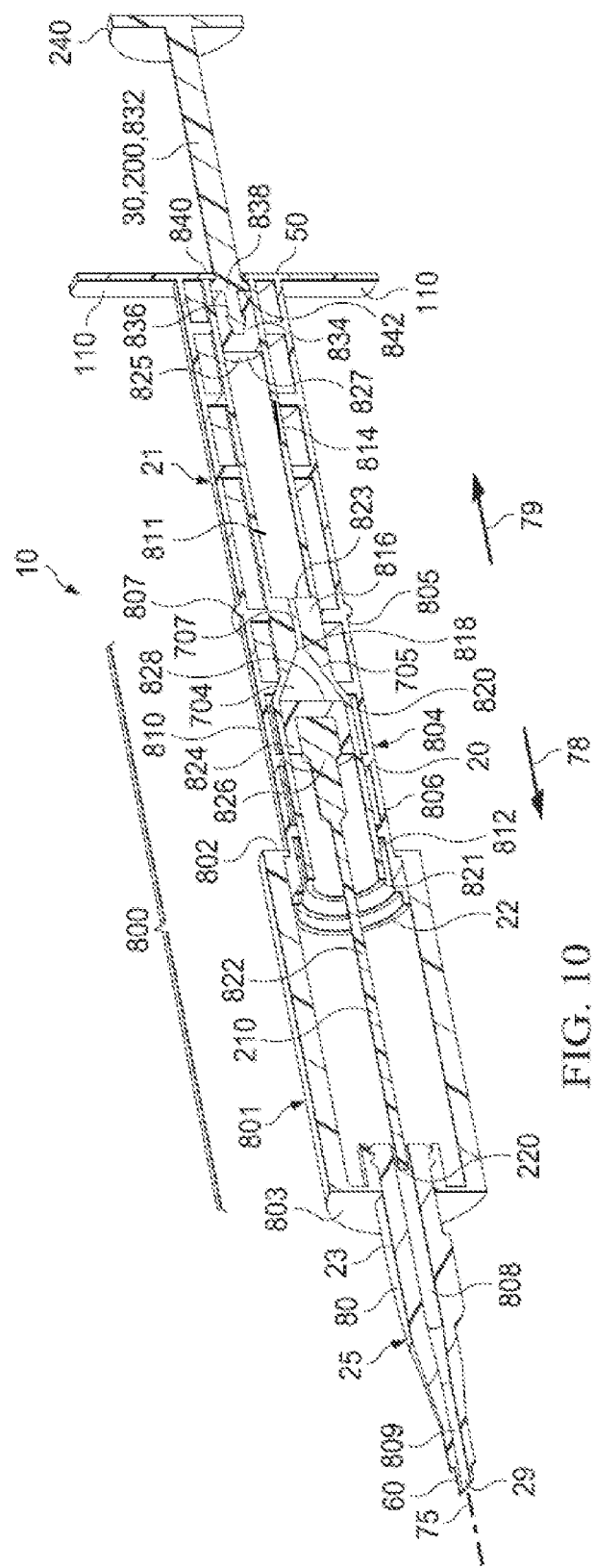
FIG. 10 is a cross-sectional view of an exemplary IOL injector having an injector body with a collapsible portion and a hydraulic damping system.

FIG. 10 is a cross-sectional view of an exemplary IOL injector 10 wherein the injector body 20 includes a collapsible portion 800 that forms a telescoping arrangement.

Although the IOL injector 10 of FIG. 10 is shown as including a hydraulic damping system (described in more detail below), in other implementations, the hydraulic damping system may be omitted from an IOL injector having a collapsible portion.

The term "telescoping" generally refers to movement of a first part sliding out from, or into, a second part, where the two parts are coupled, and have an extended or uncollapsed configuration, and a shortened or collapsed configuration. A collapsible portion may include a first part and a second part that may be in the form of sleeves having different cross-sectional sizes and that are telescopingly arranged. The sleeves may be cylindrically shaped. In some instances, the sleeves may be in the form of cylinders or tubes having circular cross-sectional shapes, and the sleeves may have different diameters such that one sleeve is slideably receivable into the other sleeve. In other implementation, the sleeves may be cylinders or tubes having non-circular cross-sectional shapes but are sizes such that one sleeve is slideably receivable into the other sleeve. The sleeves may have a concentric, or nested, arrangement in which a sleeve with a smaller cross-sectional size (i.e., "inner sleeve") is received into and coaxially arranged with a sleeve having a larger cross-sectional size (i.e., "outer sleeve"). Two or more concentrically coupled telescoping sleeves may be used in a collapsible portion. The movement of one sleeve sliding out from, or into another allows respective lengthening or shortening of the collapsible portion. The lengthened, or extended configuration may be referred to as "uncollapsed", and the shortened configuration, for example, where the length of the inner sleeve is entirely or mostly contained within the outer sleeve, may be referred to as "collapsed".

Figure 13:
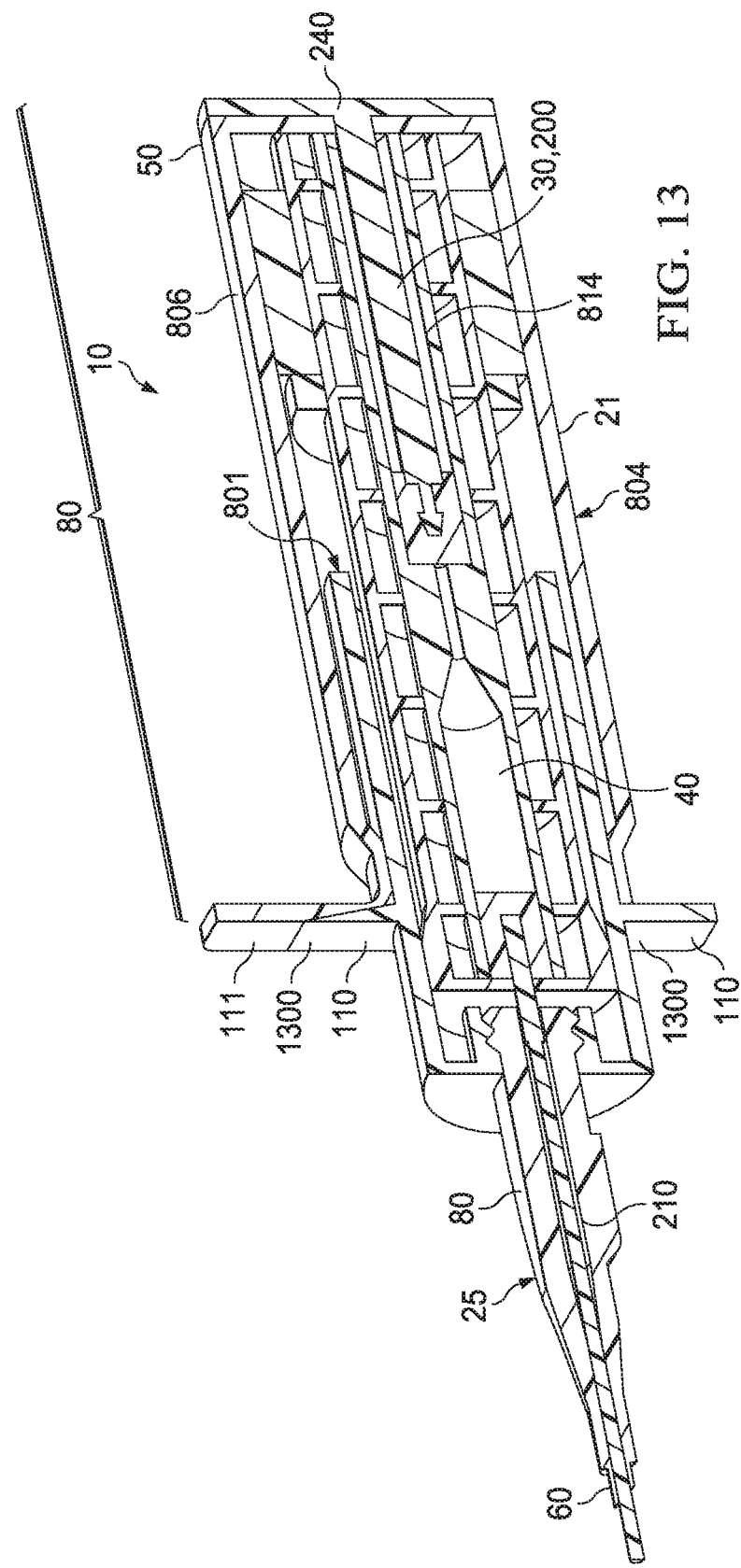
FIG. 13 is a cross-sectional view of another exemplary IOL injector in a fully actuated condition and having a collapsible portion and a hydraulic damping system.

For example, as shown in FIG. 10, the collapsible portion 800 includes a first sleeve 801 having a proximal end 802 and a distal end 803 and a second sleeve 804 having a proximal end 805 and a distal end 22. In the illustrated example, the second sleeve 804 forms a distal portion 810 of the main body 21. In other implementations, the second sleeve 804 may be separate from the main body 21. The proximal end 802 of the first sleeve 801 is slideably coupled with the distal end 22 of the second sleeve 804. In some implementations, for example as shown in FIG. 10, the first sleeve 801 forms an outer sleeve; the second sleeve 804 forms an inner sleeve; and the second sleeve 804 is concentrically arranged and slideable within the first sleeve 801, such that the distal portion 810 of the main body 21 slides concentrically within the first sleeve 801. In other implementations, for example as shown in FIG. 13, the first sleeve 801 forms an inner sleeve; the second sleeve 804 forms an outer sleeve; and the first sleeve 801 is concentrically arranged and slideable within the second sleeve 804, such that the first sleeve 801 slides concentrically within the distal portion of the main body 21. Other configurations of the collapsible portion are possible. For example, in other implementations, the collapsible portion may include more than two sleeves that are telescoping arranged.

Referring again to FIG. 10, the first sleeve 801 is concentrically arranged and slideable within the second sleeve 804. The first sleeve 801 and the second sleeve 804 may be coupled such that the second sleeve 804 is retained within the first sleeve 801 when the second sleeve 804 is fully extended from or is in the uncollapsed configuration with the first sleeve 801. For example, the first sleeve 801 and the second sleeve 804 may be slideably coupled by a slip joint.

In an uncollapsed configuration, the distal end 22 of the second sleeve 804 is adjacent to the proximal end 802 of the first sleeve 801. In a collapsed configuration, the distal end 22 of the second sleeve 804 is adjacent to the distal end 803 of the first sleeve 801. For example, in some implementations, a distance between the distal end 22 of the second sleeve 804 and the proximal end 802 of the first sleeve 801 when in an uncollapsed configuration may be 20 to 40 mm.

The main body portion 21 includes a first cylinder 812, a second cylinder 814, and a restrictor 816 disposed therebetween. The first cylinder 812, second cylinder 814, and restrictor 816 are in fluid communication with each other and, collectively, define a passage 811. The restrictor 816 includes a distal chamber 704 and an orifice 707. The distal chamber 704 and orifice 707 form a continuous passage between the first cylinder 812 and the second cylinder 814. In the illustrated example, the distal chamber 704 is flared (e.g., in the form of a cone) such that a cross-sectional size of the distal chamber increases in the distal direction from a distal end 818 of the orifice 707 to a proximal end 820 of the first cylinder 812.

As also shown in FIG. 10, the IOL injector 10 includes a two-piece plunger 30 that includes a body portion 200 and a plunger rod 210. The plunger rod 210 is slideably received in the first cylinder 812. The plunger rod 210 includes a plunger tip 220, a distal portion 822, and a seal 824 disposed at a proximal end 826 of the distal portion 822. The distal portion 822 may be rigid compared to seal 824. In the illustrated example, the distal portion 822 is received into a cavity formed by the seal 824. However, in other implementation, the distal portion 822 and the seal 824 may be joined in any way. In an initial position, a proximal end 828 of the plunger rod 210 is located at the proximal end 820 of the first cylinder 812.

The body portion 200 is slideably received into the second cylinder 814 at the proximal end 50 of the main body 21. The body portion 200 includes a rigid distal portion 832 and a seal 834 disposed at a distal end 836 of the distal portion 832. The distal portion 832 also includes a flared portion 838 disposed adjacent to the seal 834. The flared portion 838 increases in cross-sectional size in the distal direction. As shown in FIG. 10, tabs 110 define an opening 840 that is smaller in size that the cross-sectional size of the second cylinder 814. The distal end 842 of the flared portion 838 is larger than the size of the opening 840. Thus, the flared portion 838 and the opening 840 cooperate to retain the distal portion 832 of the plunger 30.

The body portion 200 is concentric with second cylinder 814. The second cylinder 814 is concentric within the main body 21. In other implementations, the one or both of the first cylinder 812 and the second cylinder 814 may be nonconcentric with main body 21. Consequently, one or both of the body portion 200 and the plunger rod 210, when received into respective first and second cylinders 812 and 814, may be nonconcentric with the main body 21 and, thus, nonconcentric with the first sleeve 801 and the second sleeve 804. In still other implementations where one or more of the sleeves of a collapsible portion are not concentric with one or more other sleeves of the collapsible portion, the plunger may be nonconcentric with one or more of the sleeves.

The main body 21 may have one or more protrusions 807 on the outer surface 806 of the main body 21. The protrusion 807 is located at the proximal end 805 of the second sleeve 804 and is adapted to contact the proximal end 802 of the first sleeve 801 when the collapsible portion 800 is in a collapsed configuration.

The proximal end 23 of the nozzle 25 is coupled to the distal end 803 of the first sleeve 801. The injector body has a bore 40 having a longitudinal axis 75 extending from the proximal end 50 of the main body 21 to the distal end 60 of the nozzle 25.

The IOL injector 10 includes a storage compartment 80 that includes an IOL storage location 808, and the nozzle 25 includes an IOL dwell location 809 distal to the IOL storage location 808. Although not show, the storage compartment may include access to an interior thereof such as via a door, which may be similar to door 90. With the collapsible portion 800 in the uncollapsed configuration, the plunger tip 220 has a first position that is proximally adjacent to the IOL storage location 808. When the collapsible portion 800 is in the collapsed configuration, the plunger tip 220 has a second position proximally adjacent to the IOL dwell location 809. Thus, when the collapsible portion 800 is collapsed, the plunger rod 210 moves relative to the first sleeve 801 and the nozzle 25 such that the plunger tip 220 engages the IOL disposed in the storage location 808 and advances the IOL to the dwell location 809. In some implementations, the plunger tip 220 may be between 5 mm to 20 mm proximal to the IOL 70 in the storage location 808 when the collapsible portion 800 is in the uncollapsed configuration, and the plunger tip 220 will typically be immediately adjacent, in contact and engaged with the trailing, or proximally oriented, haptic 450 of the IOL 70 (or a proximal edge of an optic of a two-piece IOL) in the dwell location 809 when the collapsible portion 800 is in the collapsed configuration.

However, these values are provided merely as example, and the scope of the disclosure is not limited thereto. Rather, the relative position of the plunger tip 220 and the IOL in the storage location 808 may be any desired value.

As described herein, for example, the dwell location 809 position may be indicated by positioning of the IOL 70, or part thereof, relative to a demarcation formed on the nozzle 25, such as the demarcation 1900 described above. Further, placement of the IOL in the dwell location 809 may correspond to engagement of the protrusion 807 with the proximal end 802 of the first sleeve 801, which corresponds to the collapsed configuration of the collapsible portion 800. In other implementations, relative movement of the first sleeve 801 and the second sleeve 804 that corresponds to less than the collapsed configuration may result in positioning the IOL into the dwell location 809.

In some implementations, a length of the IOL injector 10 in the collapsed configuration may be 10 to 20% shorter than the length of the IOL injector in the uncollapsed configuration. However, the scope of the disclosure is not so limited. Rather, the percentage values are provided merely as example. In other implementations, the relative lengths of an IOL injector within the scope of the present disclosure may be less than 10% or greater than 20%.

Accordingly, the IOL injector 10 is operable to advance an IOL from the storage location 808 to a dwell location 809 in an IOL injector 10 by collapsing the collapsible portion 800. In the illustrated example, collapsing the collapsible portion 800 occurs by axially sliding the distal end 22 of the second sleeve 804 from the proximal end 802 of the first sleeve 801 to the distal end 803 of the first sleeve 801. It is further noted that placement of the IOL into the dwell location 809 by collapsing the collapsing portion 800 is obtained without advancing the plunger 30.

If a user were to hold the first sleeve 801 stationary, the second sleeve 804 is moved in the direction of arrow 78 in order to collapse the collapsible portion 800. However, a user may hold the second sleeve 804 stationary and collapse the collapsible portion 800 by driving the first sleeve 801 in the direction of arrow 79. Accordingly, in collapsing the injector body 20 in this way to advance the IOL to the dwell location 809, the plunger 30 is not moved in relation to the second sleeve 804. In addition, collapsing the injector body 20 in this way results in a shorter IOL injector 10 for use in injecting the IOL 70 into the eye from the dwell location 809. The collapsible feature improves ergonomics by reducing the overall length of the IOL injector 10.

Due to the sensitivity and delicacy of ocular tissues and structures, it is important that the user be able to advance the IOL 70 through an IOL injector with an acceptable peak or maximum speed and force. In some existing IOL injectors, when folding and advancing the IOL into the eye, there is typically a high peak axial force that must be applied, e.g., by a user, just before the IOL is expelled from the IOL injector. However, as the IOL begins to emerge from the IOL injector, the force required to continue to advance the IOL rapidly reduces. As a result, in some cases, the larger change force needed to advance the IOL may cause the IOL 70 to be ejected with high velocity in a less controllable manner. For example, the user may be unable to react quickly enough to the change in resistance associated with advancement of the IOL. The changes in resistance to advancement experienced by the IOL just prior to expelling the IOL from the IOL injector and the difficulty experienced by a user in reacting quickly to these changes in resistance in order to avoid a rapid ejection of the IOL from the IOL injector may reduce user control of the IOL injector and ultimately the IOL delivery. The challenges of delivering an IOL include ensuring that the magnitude of force applied through user interaction be consistent, repeatable, and at a desirable level. It is also important to have an IOL injector that is intuitive and capable of being utilized by users having varying levels of skills and techniques.

Figure 11:
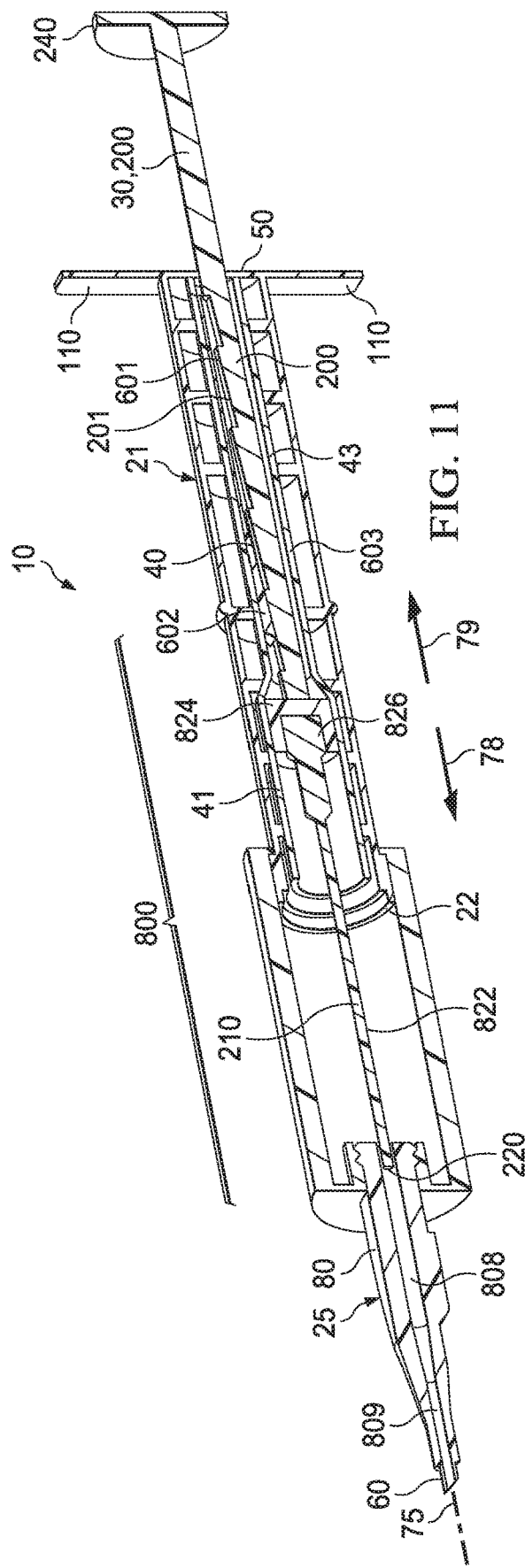
FIG. 11 is a cross-sectional view of an exemplary IOL injector having an injector body with a collapsible portion and a ribbed damping system.

The example IOL injectors 10 shown in FIGS. 10 and 11 include features for providing better control of IOL delivery, particularly during ejection of the IOL from the IOL injector. The IOL injector 10 shown in FIG. 10 includes a hydraulic damper adapted to generate smooth and controlled axial forward motion used to delivery an IOL and provide smooth damping of the axial movement. In doing so, the IOL injector 10 provides for a smooth and controlled actuation of the plunger 30 by a user.

As shown in FIG. 10, the IOL injector 10 includes a hydraulic damper that includes the first cylinder 812, the second cylinder 814, and the restrictor 816. The first cylinder 812 has a proximal end 820 and a distal end 821, and the second cylinder 814 includes a proximal end 823 and a distal end 825. In some instances, the fluid may be an incompressible fluid, such as an oil, e.g., mineral oil, water, or any other desired liquid. A fluid is disposed between the distal end 827 and a proximal end 828 of the plunger rod 210. Thus, in the condition of the IOL injector shown in FIG. 10, the fluid occupies a volume of the second cylinder 814 between the distal end 827 of the body portion 200 and the orifice 707 and distal chamber 704 of the restrictor 816.

The body portion 200 of the plunger 30 is slideably disposed within the second cylinder 814 and movable from the proximal end 825 of the second cylinder 814 to the distal end 823 of the second cylinder 814 in response to an axial force applied to the plunger body 200, for example, an axial force applied to the flange 240, in the direction of arrow 78. As explained above, the distal chamber 704 and orifice 707 of the restrictor 816 form a continuous passage between the first cylinder 812 and the second cylinder 814, allowing movement of the fluid from the second cylinder 814 to the first cylinder 812 in response to movement of the body portion 200 of the plunger 30. The plunger rod 210 is slideably disposed within the first cylinder 812 and movable from the proximal end 820 of the first cylinder 812 to the distal end 821 of first cylinder 812 in response to movement of the fluid. Movement of the plunger tip 220 from the second position proximally adjacent to the IOL dwell location 809 to a third position in which the plunger 220 may extend from the opening 29 formed in the distal end 60 of the nozzle 25 occurs in response to movement of the plunger rod 210.

In some implementations, an internal diameter of the orifice 707 may be 0.1 to 2.0 mm. However, the scope of the disclosure is not so limited. Rather, the orifice 707 may have an internal diameter that is smaller than 0.1 mm or larger than 2.0 mm. In some implementations, the orifice 707 may include a one-way valve, such that the one-way valve permits passage of the fluid through the orifice 707 in the direction of arrow 78 but prevents travel of the fluid through the orifice 707 in the direction of arrow 79.

In some implementations, a cross-sectional size of the first cylinder 812 may be different from a cross-sectional size of the second cylinder 814. For example, a cross-sectional size of the first cylinder 812 may be larger than a cross-sectional size of the second cylinder 814. In other instances, the cross-sectional size of the first cylinder 812 may be larger than the cross-sectional size of the second cylinder 814. Still further, the cross-sectional size of the first cylinder 812 may be the same as the cross-sectional size of the second cylinder 814. Where, the first and second cylinder 812 and 814 are circular in cross-section, the size of the diameter of the first cylinder 812 may be larger, smaller, or the same as the diameter of the second cylinder 814. In some instances, a ratio of an internal diameter of the second cylinder 814 to an internal diameter of the first cylinder 812 may be between 1:1 and 5:1.

Where the cross-sectional size (e.g., diameter) of the first cylinder 812 is larger the cross-sectional size (e.g., diameter) of the second cylinder 814, the ratio of the diameters of the first and second cylinders 812 and 814 may provide a mechanical advantage, such that axial movement of the plunger rod 210 in response to movement of the fluid is not equal to axial movement of the body portion 200 of the plunger 30. That is, in such instances, the plunger rod 22 moves a shorter distance within the first cylinder 812 for a given displacement of the body portion 200 of the plunger 30 within the second cylinder 814. Stated another way, where the first cylinder 812 has a larger diameter than the second cylinder 814, the plunger rod 210 would move at a faster rate through the first cylinder 812 than the main body 200 through the second cylinder 814.

In still other implementations, the diameter of the second cylinder 814 and/or the first cylinder 812 may vary along the axis longitudinal 75, such that, for a given rate of advancement of the body portion 200 or for a constant force applied thereto, the rate of advancement of the plunger rod 210 may vary. For example, when the body portion 200 is viewed as a reference frame, the plunger rod 210 may speed up and/or slow down relative to the body portion 200 where the diameters of the first cylinder 812 and/or the second cylinder 814 varies along a length thereof. For example, a diameter of the first cylinder 812 may be smaller at the proximal end 820 than at the distal end 821, such that the plunger rod 210 initially moves faster through the first cylinder 812 and slows as the proximal end of the plunger rod 210 nears the distal end 821 of the distal chamber 704 for a constant rate of advancement of the body portion 200 or a constant force applied thereto. In such implementations, the plunger tip 220 and the IOL contacted thereby would move slower as the plunger tip 220 and IOL approach the distal end 60 of the nozzle 25. Accordingly, such movement may provide greater control of injection of the IOL 70 into the eye.

In operation, a user may advance the plunger 30 by applying an axial force to the flange 240 formed on the body portion 200 of the plunger. When the supplied force is of a sufficient magnitude, the body portion 200 would begin to move distally within the second cylinder 814 in the direction of arrow 78. This movement of the body portion 200 displaces fluid within the second cylinder 814, forcing the fluid through the orifice 707. The orifice 707 increases resistance to flow of the fluid and, as a result, provides a selected level of resistance that corresponds to a force applied by the user. The amount of resistance and, therefore, the force required to move the plunger 30 may be altered by altering a cross-sectional size of the orifice 707, such as by altering a diameter of the orifice 707 where the orifice is cylindrical in nature. Further, movement of the fluid through the second cylinder 814, the orifice 707, the distal chamber 704, and the first cylinder 812 dampens movement of the plunger rod 210 and body portion 200, thereby providing a smooth advancement of the plunger 30 as experienced by the user. The seals 824 and 834 may form fluid tight seals with inner walls of the first cylinder 812 and second cylinder 814, respectively. The seals 824 and 834 may conform to an inner surface of respective first and second cylinder 812 and 814.

Although the exemplary IOL injector 20 shown in FIG. 10 includes both a hydraulic damper in combination with the collapsible portion 800, in other implementations, the collapsible portion 800 may be omitted from the IOL injector 10 while retaining the hydraulic damping system.

FIG. 13 shows another example IOL injector 10 that includes both a collapsible portion 800 and a hydraulic damper. The hydraulic damper and collapsible portion 800 operate similarly and may be configured in ways similarly as those described above. In the example shown in FIG. 13, though, the IOL injector 10 is in a fully actuated condition. The first sleeve 801 is shown fully received into the second sleeve 804, which, as explained above, operates to advance the IOL from a storage location to a dwell location. In the example of FIG. 13, the second sleeve 804 may be considered to form part of the main body 21. When the first sleeve 801 is fully received into the second sleeve 804, i.e., when the collapsible portion 800 is in the collapsed configuration, one of the tabs 110 formed on the first sleeve 801 contacts and aligns with a tab 111 formed on the second sleeve 804. The one or more tabs 110 may be adapted for placement of one or more fingers of a user. The IOL injector 10 of FIG. 13 also includes a plunger 30 similar to that of the IOL injector shown in FIG. 10. In the collapsed configuration, a body portion 200 of the plunger 30 disposed in a second cylinder 814 may be advanced by application of force to a flange 240 formed on the body portion 200. The body portion 200 is show fully advanced within the second cylinder 814, which results in displacement of fluid within the second cylinder 814 and, as a result, displacement of the plunger rod 210. The plunger rod 210 is shown fully advanced with the plunger tip extending beyond the nozzle 25. The tabs 110 are disposed along the IOL injector closer to the distal end 60 than that shown in FIG. 10. Accordingly, the IOL injector 10 may be held and actuated with two fingers engaged with distal sides 1300 of the tabs 110 and another (e.g., a thumb) on the flange 240. As a result, the user, such as a surgeon, is able to hold his hand closer to distal end 60 of the nozzle 25 and, therefore, the eye while delivering the IOL. This may provide more stability for users to hold the device steady during the delivery of the IOL 10 into an eye.

The present disclosure also relates to an IOL injector having a ribbed damper configured to provide a frictional resistance to axial advancement of the plunger 30. For example, FIG. 11 is a cross-sectional view of anther IOL injector 10 that is similar to the example shown in FIG. 10 except that the IOL injector 10 shown in FIG. 11 includes a ribbed damping system as opposed to the fluid. Although the exemplary IOL injector in FIG. 11 shows an IOL injector 10 as also having a collapsible portion 800 (which operates similarly to the collapsible portion 800 described above), the collapsible portion 800 may be omitted from the IOL injector 10 while retaining the ribbed damping system.

As shown in FIG. 11, the main body 21 defines a bore 40. In the illustrated example, the bore 40 includes a first portion 41 and a second portion 43. In the example shown, the first portion 41 has a larger cross-sectional size than the second portion 43. In other implementations, the cross-sectional sizes of the first portion 41 and the second portion 43 may be the same. Still further, in other implementations, the cross-sectional size of the first portion 41 may be smaller than the cross-sectional size of the second portion 43.

The IOL injector 11 includes a plunger 30 having a body portion 200 and a plunger rod 210. In the example shown in FIG. 11, the body portion 200 and the plunger rod 210 are separate components, and the plunger rod 210 includes a distal portion 822 and seal 824 disposed at a proximal end 826 of distal portion. The seal 824 may conform to an inner surface of the first portion 41. In other implementations, the plunger rod 210 and body portion 200 may form a unitary component. For example, in some instances, the plunger rod 210 and body portion 200 may be a single, integrally formed piece.

The second portion 43 of the bore 40 in cooperation with an exterior surface 201 of the body portion 200 defines a ribbed damper configured to provide a frictional resistance to axial displacement of the plunger 30. The ribbed damper includes at least one rib 601 formed in the exterior surface 201 of the body portion 200 and at least one rib 602 on an interior wall 603 of the second portion 43 of the bore 40. As shown, a plurality of ribs 601 is present, while a single rib 602 is present. However, the scope of the disclosure is not so limited. Rather, other implementations may include a plurality of ribs 602 in combination with a single rib 601 or a combination of a plurality of ribs 601 and a plurality of ribs 602. The at least one rib 601 on the body portion 200 is configured to contact the at least one rib 602 on the interior wall 603, and, together, the ribs 601 and 602 are adapted to provide a frictional resistance to the axial movement of the plunger 30. In some instances, the ribbed damper may be composed of flexible material, such as deformable plastic, such that contact between the ribs 601 and 602 during the axial movement of the plunger 30 causes resistance to the axial movement in the direction of arrow 78 but does not prevent axial movement in the direction of arrow 78.

As shown in FIG. 11, the ribs 601 and 602 are wedge shaped. In the case of ribs 601, the ribs 601 flare outwardly from a distal end to a proximal end. The rib 602 flares inwardly from a proximal end to a distal end. Thus, the ribs 601 and rib 602 are oppositely oriented to each other. Thus, as the plunger body 200 is advanced though the second portion 43 of the bore 40, each of the ribs 601 pass the rib 602. A resistance force increase from an initial engagement of one of the rib 601 and the rib 602 to a maximum value where the distal end of the rib 601 is adjacent to the proximal end of rib 602. Thus, as each of the rib 601 moves past the rib 602, interference between the two increases, thereby causing an increase in the resistance to the axial advancement of the plunger 30.

Figure 12:
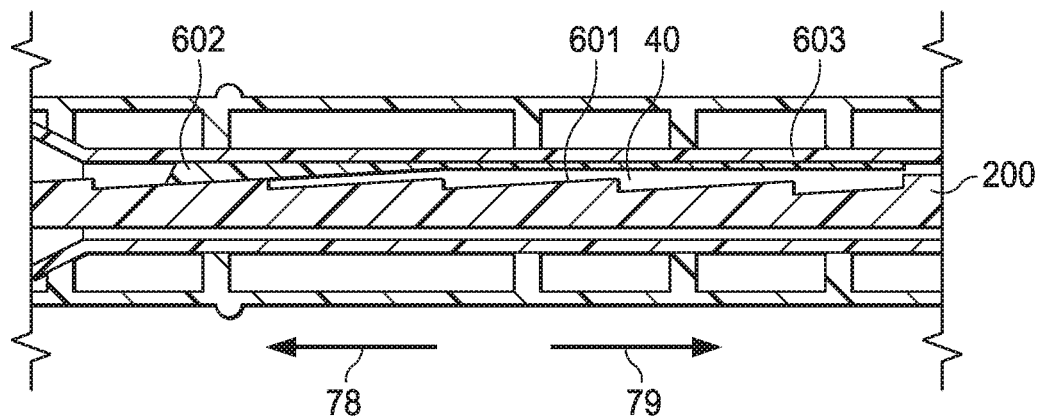
FIG. 12 is a detail view of an exemplary ribbed damping system.
Figure 14:
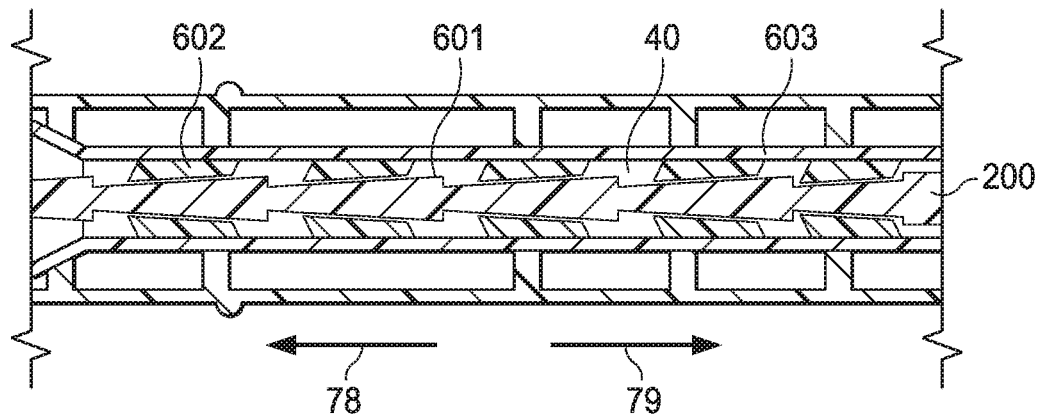
FIG. 14 is a detail view of another exemplary ribbed damping system.
Figure 15:
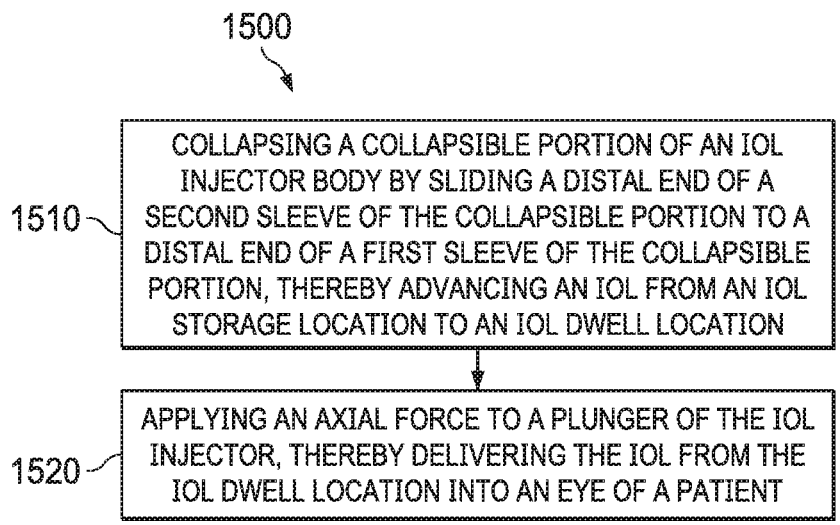
FIG. 15 is an example method of using an IOL injector.

FIG. 12 and FIG. 14 are cross-sectional detail views of exemplary ribbed dampers. FIG. 12 is a detail view of the ribbed damper shown in FIG. 11 and operates similarly. FIG. 14 shows a body portion 200 of a plunger 30 that includes ribs 601 on opposing sides thereof. In some instances, the ribs 601 may be a series of conical sections that extend circumferentially around the body portion 200, e.g., 360° or some angular amount less than 360°. The ribs 602 may be in the form of a series of teeth formed adjacent to the opposing sides of the body portion 30 on which ribs 601 are disposed, or, in other instances, may encircle all or a portion of the second portion 43 of the bore 40 where the ribs 601 encircle all or a portion of the body portion 200. As shown in FIGS. 12 and 14, in some implementations, one or more of the ribs 601 on the body portion 200 of the plunger 30 may form a ridge and one or more ribs 602 on the interior wall 603 may form a ridge-engaging tooth, such that, interaction of the ridge and ridge-engaging tooth permit movement of the body portion 220 of plunger 30 in the direction of arrow 78 but prevent movement of the distal end 220 of the plunger 30 in the direction of arrow 79.

In some implementations, the one or more ribs 601 and/or 602 may be a plurality of ribs 601 and/or 602, and the distance between each of the ribs 601 and/or 602 may decrease with decreasing distance from the distal end of the main body 200. Accordingly, having a closer placement of the ribs 601 and/or 602 toward the distal end of the body portion 200 and/or interior wall 603 of the bore 40 may provide increased resistance to counteract the typically high peak axial force and the large pressure release when the IOL 70 passes through the exit of the distal tip 27.

In any of the implementations described herein, the components of the IOL injectors may be combined with one another. For example, the IOL injector having the hydraulic damper may also include the ribbed damper. The injector body having the hydraulic damper or the ribbed damper may also include the collapsible portion. The collapsible portion may include at least two sleeves, a first sleeve having a proximal end and a distal end, and a second sleeve having a proximal end and a distal end. The first sleeve may be slideably coupled with the second sleeve, and a nozzle having a proximal end and a distal end may be coupled to the distal end of the first sleeve of the collapsible portion.

Accordingly, the present disclosure is encompasses methods of using the IOL injectors herein described. For example, the example method 1500 includes the steps of (a) collapsing a collapsible portion of an IOL injector body by sliding a distal end of a second sleeve of the collapsible portion to a distal end of a first sleeve of the collapsible portion, thereby advancing an IOL from an IOL storage location to an IOL dwell location at 1510; and (b) applying an axial force to a plunger of the IOL injector, thereby delivering the IOL from the IOL dwell location into an eye of a patient at 1520.

Various implementations of the IOL injectors described herein and within the scope of the present disclosure may be configured to deliver an IOL base and/or an IOL optic of a multi-piece IOL, or a one-piece IOL. Various implementations of the IOL injectors and associated methods described herein may be used with an IOL base and/or an optic that are manually loaded into the IOL injector by a user or preloaded therein prior to delivery by a user.

Advantages of the IOL injectors described herein include but are not limited to the following. The collapsible portion of the injector body allows the initial movement of the IOL to the dwell location by collapsing a portion of the injector body. This feature shortens the overall length of the IOL injector and improves the usability and ergonomics of the device. The IOL injectors having the hydraulic or ribbed dampers described herein allow for smooth control of axial motion of the plunger during delivery of an IOL to an eye. This may mitigate incidences of sudden IOL ejection and may reduce user fatigue associated with applying a constant force for a longer period of time.

The above-disclosed subject matter is to be considered illustrative, and not restrictive, and the appended claims are intended to cover all such modifications, enhancements, and other implementations that fall within the true spirit and scope of the present disclosure. Thus, to the maximum extent allowed by law, the scope of the present disclosure is to be determined by the broadest permissible interpretation of the following claims and their equivalents and shall not be restricted or limited by the foregoing detailed description.

The invention claimed is:

1. An intraocular lens (IOL) injector having a collapsible injector body configured to reduce a length of the IOL injector upon an advancement of an IOL from a storage location to a dwell location, the IOL injector comprising:
   an injector body comprising:
      a main body having a proximal end and a distal end and defining a passage therethrough;

an IOL storage compartment, the storage compartment adapted to store an IOL in a storage location;
a nozzle coupled to the distal end of the main body, the nozzle comprising:
a bore; and
a distal opening in fluid communication with the bore; and
a collapsible portion disposed between the main body and the nozzle, the collapsible portion moveable between a collapsed configuration and an uncollapsed configuration and comprising:
a first sleeve; and
a second sleeve telescopingly received into the first sleeve;
a plunger received into and movably within the injector body, the collapsible portion moveable from the uncollapsed configuration in which the first sleeve is at a first position relative to the second sleeve to the collapsed configuration in which the first sleeve is at a second position relative to the second sleeve and a plunger tip moveable from a first plunger tip location to a second plunger tip location distal of the first plunger tip location when the collapsible portion is moved from the uncollapsed configuration to the collapsed configuration; and
a hydraulic damper disposed within the injector body, the hydraulic damper comprising:
a first cylinder;
a second cylinder; and
a restrictor, the restrictor disposed between the first cylinder and the second cylinder, wherein restrictor comprises an orifice in fluid communication with the first cylinder and the second cylinder, wherein the plunger comprises a body portion received and slideable within the second cylinder and the plunger tip received and slideable with the first cylinder, and wherein the hydraulic damper further comprises a fluid disposed between a proximal end of the plunger rod and a distal end of the body portion.

2. The IOL injector of claim 1, wherein the first plunger tip position is proximal to the storage location and wherein the plunger tip is adapted to engage an IOL disposed in the storage location and move the IOL from the storage location within the storage compartment to a dwell location within the nozzle when the collapsible portion is moved from the uncollapsed configuration to the collapsed configuration.

3. The IOL injector of claim 1, wherein the second sleeve is concentrically disposed within the first sleeve.

4. The IOL injector of claim 1, wherein the first cylinder has a first cross-sectional size and wherein the second cylinder has a second cross-sectional size.

5. The IOL injector of claim 4, wherein the first cross-sectional size is larger than the second cross-sectional size.

* * * * *